(12) United States Patent
Hiltz (10) Patent No.: US 9,687,715 B1
(45) Date of Patent: Jun. 27, 2017

(54) SYSTEMS AND METHODS FOR A GOLFER TO DETERMINE TOOLS AND TRAINING REGIMENS THAT BEST ASSIST THE GOLFER TO IMPROVE GOLF SWING

(71) Applicant: Neil Richard Hiltz, El Granada, CA (US)

(72) Inventor: Neil Richard Hiltz, El Granada, CA (US)

( * ) Notice: Subject to any disclaimer, the term of this patent is extended or adjusted under 35 U.S.C. 154(b) by 242 days.

(21) Appl. No.: 14/794,658

(22) Filed: Jul. 8, 2015

Related U.S. Application Data (60) Provisional application No. 62/024,939, filed on Jul. 15, 2014.

(51) Int. Cl.
| | | |
|---|---|---|
| *A63F 9/24* | (2006.01) | |
| *A63B 69/36* | (2006.01) | |
| *G06F 17/30* | (2006.01) | |
| *H04L 29/08* | (2006.01) | |
| *G06F 3/0482* | (2013.01) | |

(52) U.S. Cl.
CPC ............ *A63B 69/36* (2013.01); *G06F 3/0482* (2013.01); *G06F 17/3053* (2013.01); *G06F 17/30554* (2013.01); *G06F 17/30592* (2013.01); *G06F 17/30867* (2013.01); *H04L 67/02* (2013.01)

(58) Field of Classification Search
USPC ................................................ 463/3; 700/91
See application file for complete search history.

(56) References Cited

U.S. PATENT DOCUMENTS

| | | | | |
|---|---|---|---|---|
| 9,261,526 | B2 * | 2/2016 | Bentley | A61B 5/11 |
| 9,384,671 | B2 * | 7/2016 | Krosky | G09B 5/02 |
| 2013/0102419 | A1 * | 4/2013 | Jeffery | A63B 69/00 |
| | | | | 473/409 |
| 2014/0260635 | A1 * | 9/2014 | Leech | G09B 19/0038 |
| | | | | 73/645 |
| 2014/0274240 | A1 * | 9/2014 | Meadows | A63F 13/216 |
| | | | | 463/3 |
| 2015/0018112 | A1 * | 1/2015 | Millers | A63B 69/3623 |
| | | | | 473/224 |
| 2015/0352404 | A1 * | 12/2015 | Schwenger | A63B 24/0003 |
| | | | | 700/91 |

\* cited by examiner

*Primary Examiner* — Masud Ahmed
(74) *Attorney, Agent, or Firm* — Plager Schack LLP (57) ABSTRACT

A process and system are disclosed that identifies tools and training regimens that best assist the golfer to improve the golfer's own golf swing and golf game. The process and system provide personal perspective on clubs, training aids, and instructors, as well as provide a data-driven, fact-based review of each training mode and method among several crowd-sourced globally-used training modes and methods of other golfers. The process and system identify a set of best practices for the golfer to improve golf swing and golf game based on scaled insights derived from the crowd-sourced golf information in light of the personal perspective on clubs, training aids, and instructors. In some embodiments, the system and process are implemented as a website and software applications that allow golfers to interact with the system and perform the methods in order to improve golf swing and golf game.

8 Claims, 4 Drawing Sheets

SYSTEMS AND METHODS FOR A GOLFER TO DETERMINE TOOLS AND TRAINING REGIMENS THAT BEST ASSIST THE GOLFER TO IMPROVE GOLF SWING

CLAIM OF BENEFIT TO PRIOR APPLICATION

This application claims benefit to U.S. Provisional Patent Application 62/024,939, entitled "SYSTEMS AND METHODS FOR A GOLFER TO DETERMINE TOOLS AND TRAINING REGIMENS THAT BEST ASSIST THE GOLFER TO IMPROVE GOLF SWING," filed Jul. 15, 2014. The U.S. Provisional Patent Application 62/024,939 is incorporated herein by reference.

BACKGROUND

Embodiments of the invention described in this specification relate generally to systems for the improvement of athletic performance, and more particularly, to systems that assist in the identification of tools and training regimens that help a golfer improve golf swing performance.

Current systems for golf swing and game improvement are small scale, based on opinion, or are biased. In short, there is no scaled, neutral methodology for defining the best path to improve a golfer's golf swing and golf game. Existing golf improvement methodologies are not suitable for most golfers to be able to predictably improve their golf swing and game. For instance, some methodologies are entirely tailored to be personal for each individual golfer (e.g., working with a swing coach) which provides only limited help for a small portion of golfers who happen to work well with a swing coach and who happen to have golf swing problems which the swing coach is able to address and correct. Other systems and/or methodologies are either biased (e.g., based on fake reviews or celebrity endorsements of training aids) or are not based on significant amounts of real world performance improvement results.

Therefore, what is needed is a system and/or methodology that allows continued personal perspective on clubs, training aids, and instructors, and also provides a data-driven, fact-based review of all training modes and methods globally in order to identify a set of best practices based on scaled insights.

BRIEF DESCRIPTION

Some embodiments of the invention include a novel process for identifying golf-improving tools and training regimens and a novel golf tool and training regimen ranking system that provides personal perspective on clubs, training aids, and instructors to assist a golfer in identifying tools, instructors, and training regimens that best improve the golfer's own golf swing and golf game. In some embodiments, the process for identifying golf-improving tools and training regimens provides a data-driven, fact-based review of each training mode and method among several crowd-sourced globally-used training modes and methods. In some embodiments, the process identifies a set of best practices for the golfer to improve golf swing and golf game based on scaled insights derived from the crowd-sourced golf information in light of the personal perspective on clubs, training aids, and instructors.

In some embodiments, the golf tool and training regimen ranking system includes a plurality of cloud-network data repositories accessed over public communication network by a plurality of user computing devices, a set of golf tool and training regimen crowd-sourcing and analysis computing devices associated with the plurality of cloud-network data repositories, and a golf tool and training regimen ranking server computing device that ranks and provides personal perspectives on golf clubs, training aids, and instructors.

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodiments described by this document, a full review of the Summary, Detailed Description, and Drawings is needed. Moreover, the claimed subject matters are not to be limited by the illustrative details in the Summary, Detailed Description, and Drawings, but rather are to be defined by the appended claims, because the claimed subject matter can be embodied in other specific forms without departing from the spirit of the subject matter.

BRIEF DESCRIPTION OF THE DRAWINGS

Having described the invention in general terms, reference is now made to the accompanying drawings, which are not necessarily drawn to scale, and wherein.

DETAILED DESCRIPTION

In the following detailed description of the invention, numerous details, examples, and embodiments of the invention are described. However, it will be clear and apparent to one skilled in the art that the invention is not limited to the embodiments set forth and that the invention can be adapted for any of several applications.

Some embodiments of the invention include a novel process for identifying golf-improving tools and training regimens and a novel golf tool and training regimen ranking system that provides personal perspective on clubs, training aids, and instructors to assist a golfer in identifying tools, instructors, and training regimens that best improve the golfer's own golf swing and golf game. In some embodiments, the process for identifying golf-improving tools and training regimens provides a data-driven, fact-based review of each training mode and method among several crowd-sourced globally-used training modes and methods. In some embodiments, the process identifies a set of best practices for the golfer to improve golf swing and golf game based on scaled insights derived from the crowd-sourced golf information in light of the personal perspective on clubs, training aids, and instructors.

In some embodiments, the golf tool and training regimen ranking system includes a plurality of cloud-network data repositories accessed over public communication network by a plurality of user computing devices, a set of golf tool and training regimen crowd-sourcing and analysis computing devices associated with the plurality of cloud-network data repositories, and a golf tool and training regimen ranking server computing device that ranks and provides personal perspectives on golf clubs, training aids, and instructors.

As stated above, current systems for golf swing and game improvement are small scale, based on opinion, or are biased. In short, there is no scaled, neutral methodology for defining the best path to improve a golfer's golf swing and golf game. Existing golf improvement methodologies are not suitable for most golfers to be able to improve their golf swing and game.

Embodiments of the process for identifying golf-improving tools and training regimens and the golf tool and training regimen ranking system described in this specification solve such problems by providing personal perspective on clubs, training aids, and instructors to assist a golfer in identifying tools, instructors, and training regimens that best improve the golfer's own golf swing and golf game. In some embodiments, the process is implemented as a software application that identifies tools, instructors, and training regimens that improve the golfer's swing and game.

In this specification, there are several descriptions of methods and processes. However, it should be noted that for the purposes of the embodiments described in this specification, the word "method" is used interchangeably with the word "process". Methods are described, therefore, by reference to example processes that conceptually illustrate process steps for identifying golf-improving tools and training regimens in relation to the golf tool and training regimen ranking system described in this specification.

Figure 1:
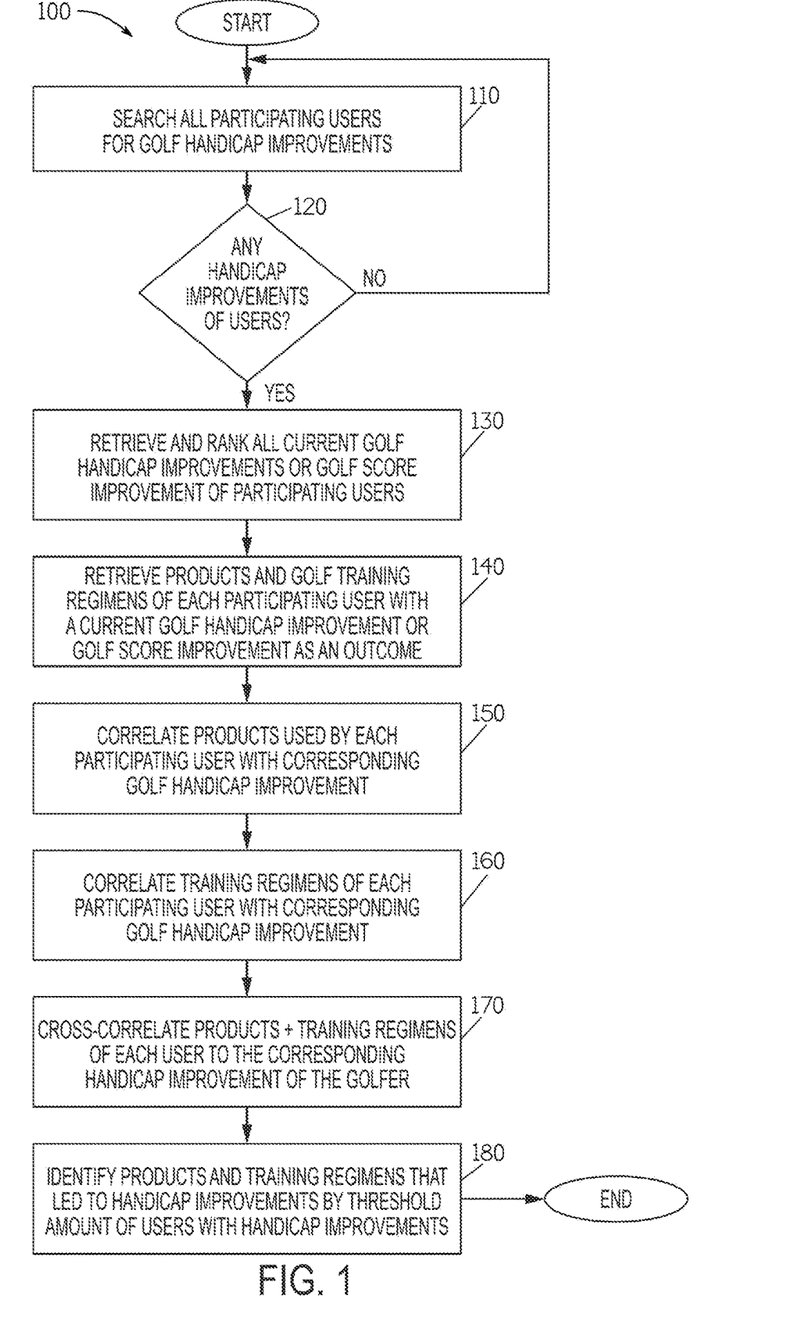
FIG. 1 conceptually illustrates a process for identifying golf-improving tools and training regimens in some embodiments.

By way of example, FIG. 1 conceptually illustrates a process 100 for identifying golf-improving tools and training regimens. In some embodiments, the process 100 is performed by a golf improvement software application. As shown in this figure, the process 100 initially searches (at 110) for golf improvements among all participating users. Participating users include, for example, golfers who are registered with an account in the system and who provide personal perspectives on golf tools, training regimens, and instructors, as well as quantifiable data, such as golf handicap, etc.

Next, the process 100 determines (at 120) whether there are any golf improvements for any of the participating users. For instance, the search may include a search of several crowd-sourced databases in which participating users provide their personal perspectives and golf scores, handicap values, etc. When the process 100 does not determine that any of the participating users have any golf improvements, the process 100 reverts back to 110 to search again. On the other hand, when the process 100 identifies improvements of one or more golfer in the system, the process 100 then retrieves and ranks (at 130) all current golf improvements of participating users. For example, there may have been improvements in golf scores, but not golf handicap. Alternatively, in another example, there may have been improvements in both golf scores and golf handicap. Any golf improvements (singularly or in combination) would be identified by the process 100 for retrieval and ranking.

In some embodiments, the process 100 then retrieves (at 140) products and golf training regimens of each participating user with a current golf handicap improvement or golf score improvement as an outcome. In some embodiments, the process 100 also retrieves the golfer-specific personal perspectives associated with the retrieved products and golf training regimens. In some embodiments, the process 100 correlates (at 150) the products used by each participating user with corresponding golf improvements. In some embodiments, the process 100 also correlates (at 160) training regimens of each participating user with corresponding golf improvements. Then the process 100 of some embodiments cross-correlates (at 170) products and training regimens of each participating user to the corresponding golf improvement of the golfer. After completing these analysis steps, the process 100 of some embodiments identifies (at 180) products and training regimens that led to golf improvements (e.g., golf score, golf handicap, etc.). In some embodiments, each golf improvement identified by the process 100 needs to satisfy a threshold amount of improvement. For instance, a golf score improvement of at least five percent better than the golfer's personal best, or at least five percent better than the golfer's average score, etc. In some embodiments, after the products and training regimens are identified, the process 100 ends.

As noted above, the process for identifying golf-improving tools and training regimens can be implemented as software which runs on a computing device and allows a participating user to interact with the system. In some embodiments, the software application generates a user interface for a golfer to interact with the system. In some embodiments, the user interface comprises a website for the golfer to interact within the system. In some embodiments, the system improves the golfer's golf swing and game by documenting the golfer's practice, instructors, training aids, and other methods for golf improvement. In some embodiments, the website is hosted on a cloud-network computing device that allows any and all golfers in the world to join the system in order to improve golf swing and game. In some embodiments, the website allows each golfer to provide one or more personal qualitative assessments of the clubs, instructors, and training aids.

In some embodiments, the process performs a set of operations implemented by the software application to review all golfers and determine the best instructors, training aids, and game improvement methods to improve golf swing of each individual golfer. In some embodiments, the system retrieves and uses crowd-sourced data in providing comprehensive neutral qualitative assessments that enhances a golfer's ability to improve golf swing quickly and efficiently. In some embodiments, the qualitative assessments can improve a golfer's swing and game in as fast of a way as possible. In some embodiments, the process ranks the best instructors, training aids, and regimens.

Figure 2:
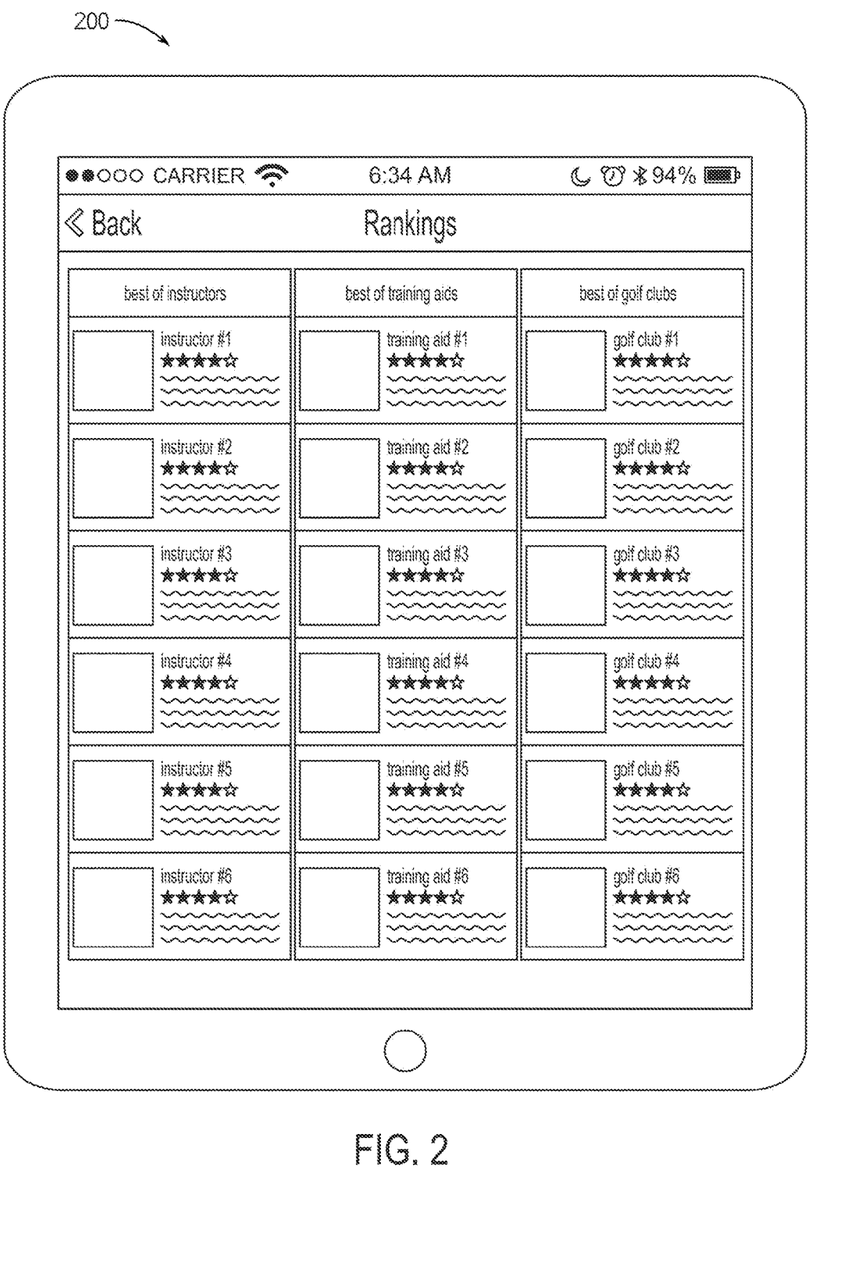
FIG. 2 conceptually illustrates a graphical user interface (GUI) of a golf tool and training regimen ranking application displayed on a mobile device of a golf tool and training regimen ranking system in some embodiments.

In some embodiments, the process displays the rankings on the website. The website can be accessed by any participating user, for example, by a computer using an Internet-accessible browser program, or by a mobile device using an Internet-accessible mobile app. By way of example, FIG. 2 conceptually illustrates a graphical user interface (GUI) of a golf tool and training regimen ranking application 200 displayed on a mobile device of a participating golfer. As shown in this figure, the GUI of the golf tool and training regimen ranking application 200 is displaying a list of best instructors, a list of best training aids, and a list of best golf clubs, along with personal perspectives of the golfers who provided their input in relation to one or more area of golf improvement (e.g., golf score improvement, golf handicap improvement, etc.). In this way, the ranked lists of instructors, training aids, and golf clubs can be reviewed by the golfer in determining ways to improve one or more aspects of their own golf game.

Embodiments of the process and the golf tool and training regimen ranking system differ from and improve upon currently existing options. In particular, some embodiments of the process and the golf tool and training regimen ranking system differ because there is no aggregated, neutral system to assess golfers and game improvement. In contrast, the process and the golf tool and training regimen ranking system of the present disclosure scale to leverage the insights of every golfer worldwide to determine the fastest possible path to game improvement. In addition, some embodiments of the process and the golf tool and training regimen ranking system improve upon the currently existing options because the existing systems and methodologies depend exclusively on knowledge of individuals and opinions, instead of objective facts and best practices determined at scale. The process and the golf tool and training regimen ranking system are based on facts and scaled best practices in ways that allow for continued personal perspective on clubs, training aids, and instructors. and, in addition, provide a data-driven, fact based review of all training modes and methods globally to provide the set of best practices based on scaled insights.

The golf tool and training regimen ranking system of the present disclosure may be comprised of the following elements. This list of possible constituent elements is intended to be exemplary only and it is not intended that this list be used to limit the golf tool and training regimen ranking system of the present application to just these elements. Persons having ordinary skill in the art relevant to the present disclosure may understand there to be equivalent elements that may be substituted within the present disclosure without changing the essential function or operation of the golf tool and training regimen ranking system.

1. A set of cloud-network data repositories accessible over public communication network by multiple user computing devices associated with multiple golfers (e.g., a products database, a reviews database, a performance database, an instructors database, a practice database, a rankings database, etc.).

2. A set of golf tool and training regimen crowd-sourcing and analysis computing devices associated with the set of cloud-network data repositories.

3. A golf tool and training regimen ranking server computing device which may host a website that provides an interface for each golfer who uses the system.

4. Software that implements the process for identifying golf-improving tools and training regimens by performing instructions that carry out operations of the process when running on a processor of a computing device (e.g., smartphone, tablet, laptop, computer, etc.), including ranking golf clubs, training aids, and instructors and providing personal perspectives on golf clubs, training aids, and instructors.

Figure 3:
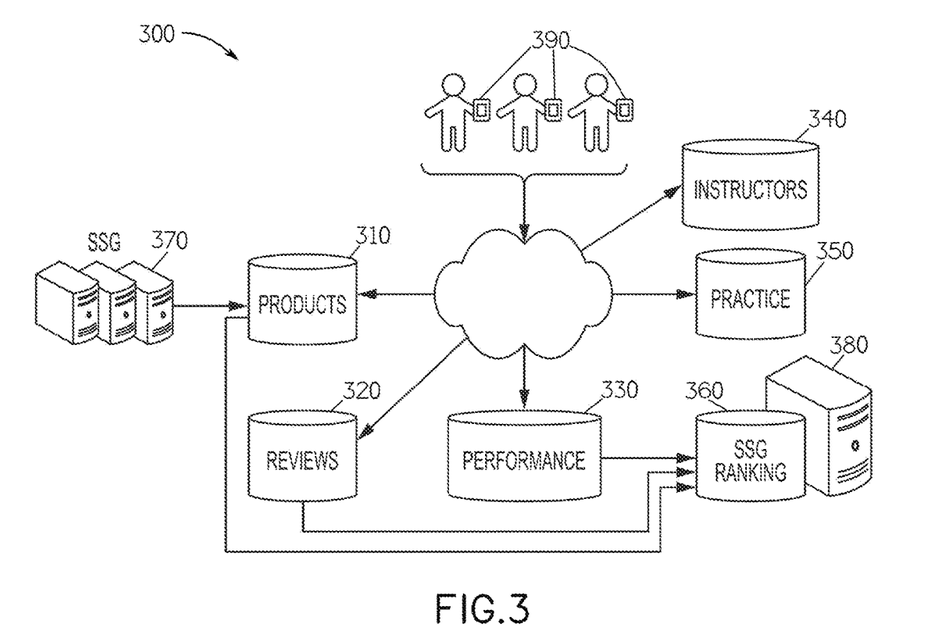
FIG. 3 conceptually illustrates an architecture of a golf tool and training regimen ranking system in some embodiments.

By way of example, FIG. 3 conceptually illustrates an architecture of a golf tool and training regimen ranking system 300 in some embodiments. As shown in this figure, the golf tool and training regimen ranking system 300 includes a products database 310, a reviews database 320, a performance database 330, an instructors database 340, a practice database 350, a rankings database 360, a set of golf tool and training regimen crowd-sourcing and analysis computing devices 370, and a golf tool and training regimen ranking server computing device 380. The golf tool and training regimen ranking server computing device 380 may host a website that provides an interface that is displayed on a set of user computing devices 390 associated with a set of golfers who uses the system 300. The set of user computing devices 390 may be mobile devices that access the system 300 over the Internet (e.g., the "cloud"). The golf tool and training regimen ranking server computing device 380 may also run the software that implements the process for identifying golf-improving tools and training regimens. The website and software work interchangeably for each golfer accessing the system 300 via their computing device 390. Since the databases 310-360, the set of golf tool and training regimen crowd-sourcing and analysis computing devices 370, and the golf tool and training regimen ranking server computing device 380 are all cloud-based systems accessible over the Internet, the system 300 essentially allows any golfer to access the system 300 at any time from virtually any location (e.g., by mobile device). For instance, a golfer may have a smartphone present during a golf practice session, and the smartphone may include a mobile application that seamlessly connects to the golf tool and training regimen ranking server computing device 380 and displays the website, thereby allowing the golfer to provide information about the golfer's golf equipment and practice methods/modes. The software running on the golf tool and training regimen ranking server computing device 380 may then perform operations for data to be collected, aggregated, and translated into best practices.

The following example describes how a golfer may use the software that implements the process to interact with the system. Initially, for example, the golfer may install software (such as a mobile app or desktop computer software application), if not already installed, and then launch (starts) the software on his or her computing device (e.g., one of the user computing devices 390). The software may provide an interface in a display of the website hosted by the golf tool and training regimen ranking server computing device 380. Instead of installing software, or in conjunction with installing the software, the golfer may simply interact with the system 300 by using a web browser to access the website hosted by the golf tool and training regimen ranking server computing device 380. When a connection to the website is made, the golfer may log into the system 300. On the other hand, if the golfer is not already a golf improvement system member (e.g., a golfer with a registered account in the system 300, or rather, a "participating" member), the golfer may first sign up (register) for an account with the system 300 through the website/application and then log into the system 300. The golfer may then input personal golf information, including their clubs, practice equipment, instructor(s), and other methods and modes that may apply, Typically, any newly registering golfer does this initially after sign up, but may periodically revisit this operation to update the personal golf information over time. The golfer may also input their personal perspective on their equipment, training aids, and instructor(s) in a manner provided by the website. For instance, the website may provide a tool for the golfer to select a score value within a range of score values (e.g., a drop down list of selectable value from 1-5) and may provide a GUI text input field in which the golfer can provide free form comments related to their perspective.

After data input by the golfer, the system 300 may then aggregate and store the data associated with the golfer-provided information (i.e., the personal golf information and the golfer's perspective data). In order to track improvements and progress of the golfer, the system 300 may evaluate the aggregated data in relation to previously aggregated and stored golfer data, by retrieval from one or more of the databases 310-360. The golf tool and training regimen ranking server computing device 380 may access one or more of the databases 310-350 by way of one or more of the golf tool and training regimen crowd-sourcing and analysis computing devices 370.

The system 300 provides qualitative assessments of the equipment, training aid, instructor(s), and so on to the computing device 390 of the golfer. In order to identify one or more best practices, the system 300 correlates tracked improvements and/or golf progress over time to time-related changes in specific areas of the golfer information. For example, if a set of golfers average a handicap of 18 over a twelve month period and then go from 18 handicap to 5 handicap in the next five months, the system 300 may evaluate the information provided by each golfer and identify a common change at a similar time in which each golfer switched from using one type of common golf club to another type of common golf club. The common information is then aggregated into a best practice. The system 300 displays the best practice in the website or in the interface of the software running on the golfer's computing device 390 and/or transmits the best practice to the golfer by some other electronic channel (e.g., via email, SMS text message, social network posting, etc.).

Note that the golfer can log into the system 300 and review aggregated information on the website or via the software at any time. Thus, any qualitative assessments conducted by the system 300 or any best practices identified by the system 300 can be viewed by the golfer at any time. For instance, the golfer can review several best practices that have been identified over months or years and get a picture of the changes made and improvements seen in the golfer's swing and/or game during that time period.

To make the process and system of the present disclosure, a person may develop the user or client-side software that runs on the computing device of the golfer and/or server-side software that runs on the server. The software may be developed to run on any of several different computing device platforms, including mobile computing devices, such as smartphones, tablets, laptop computers, etc., and stationary computing devices, such as desktop and server computers. The person may also develop the website and deploy on any of several computing device platforms that are accessible over a public network, such as the Internet. For instance, the website may be developed and deployed on a dedicated server associated exclusively with the golf improvement system, or alternatively, may be deployed on a cloud computing device provided by a commercial operator of a cloud service computing system. In some cases, the website may be developed with a web server application that routes traffic from client computing devices to the website. In some cases, the web server application may operate on a computing device which also includes the website. In other cases, the website is deployed on a computing device separate from a computing device on which the web server application is deployed. In addition, the person may incorporate a variety of communication routines in the software and/or website in order to communicate through a variety of electronic technological channels, including, for example, email, SMS, social network (via one or more application programmer interface(s) (API) that may be proprietary and/or open source), and other channels.

Some embodiments of the process and system, and the associated software and website, could be adapted to provide evaluation and best practices in relation to distinct golf and non-golf areas, such as golf courses, clothing, shoes, and other types of non-training equipment. This would allow the website to be a "one-stop" shop for advice. Additionally, the process and system may include e-commerce functionality, so that products can be purchased from the site/app directly.

Many of the above-described features and applications are implemented as software processes that are specified as a set of instructions recorded on a computer readable storage medium (also referred to as computer readable medium or machine readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the term "software" is meant to include firmware residing in read-only memory or applications stored in magnetic storage, which can be read into memory for processing by a processor. Also, in some embodiments, multiple software inventions can be implemented as sub-parts of a larger program while remaining distinct software inventions. In some embodiments, multiple software inventions can also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

Figure 4:
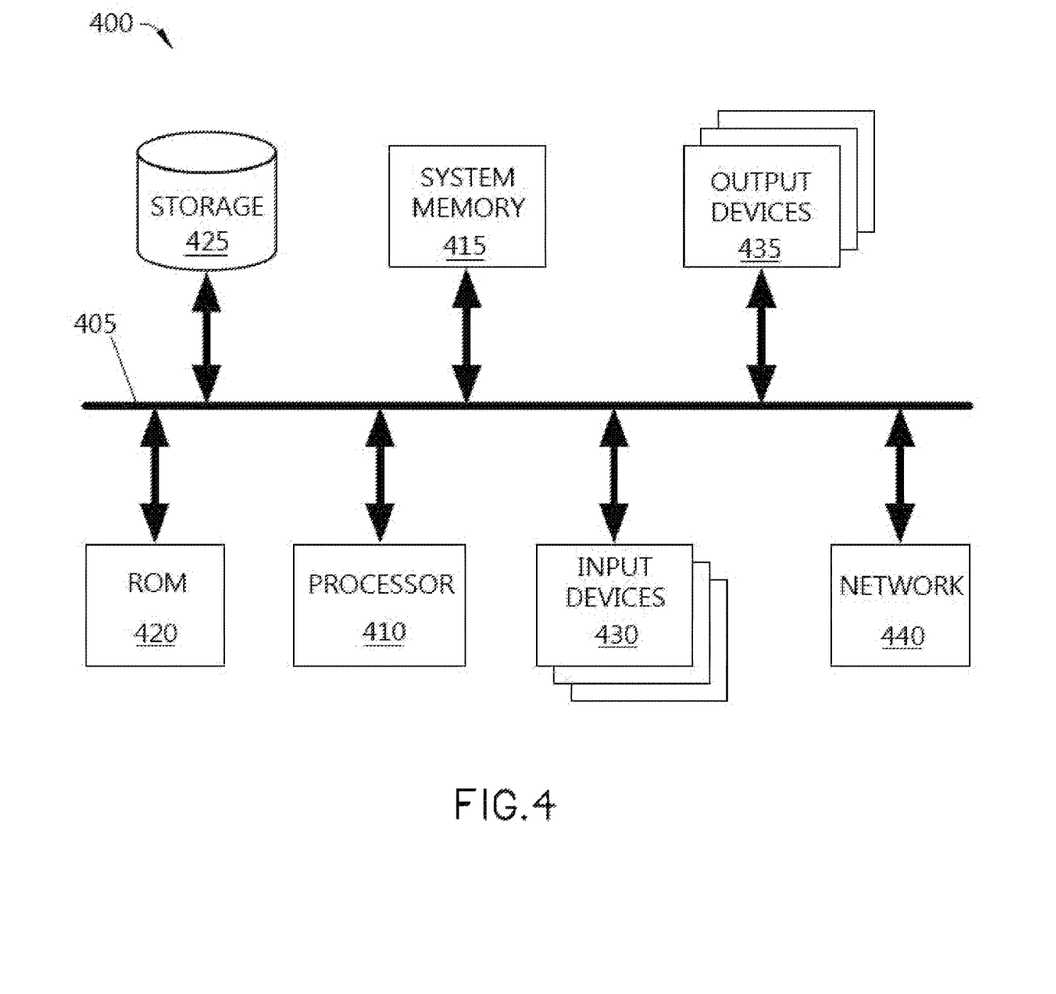
FIG. 4 conceptually illustrates an electronic system with which some embodiments of the invention are implemented.

FIG. 4 conceptually illustrates an electronic system 400 with which some embodiments of the invention are implemented. The electronic system 400 may be a computer, phone, PDA, or any other sort of electronic device. Such an electronic system includes various types of computer readable media and interfaces for various other types of computer readable media. Electronic system 400 includes a bus 405, processing unit(s) 410, a system memory 415, a read-only 420, a permanent storage device 425, input devices 430, output devices 435, and a network 440.

The bus 405 collectively represents all system, peripheral, and chipset buses that communicatively connect the numerous internal devices of the electronic system 400. For instance, the bus 405 communicatively connects the processing unit(s) 410 with the read-only 420, the system memory 415, and the permanent storage device 425.

From these various memory units, the processing unit(s) 410 retrieves instructions to execute and data to process in order to execute the processes of the invention. The processing unit(s) may be a single processor or a multi-core processor in different embodiments.

The read-only-memory (ROM) 420 stores static data and instructions that are needed by the processing unit(s) 410 and other modules of the electronic system. The permanent storage device 425, on the other hand, is a read-and-write memory device. This device is a non-volatile memory unit that stores instructions and data even when the electronic system 400 is off. Some embodiments of the invention use a mass-storage device (such as a magnetic or optical disk and its corresponding disk drive) as the permanent storage device 425.

Other embodiments use a removable storage device (such as a floppy disk or a flash drive) as the permanent storage device 425. Like the permanent storage device 425, the system memory 415 is a read-and-write memory device. However, unlike storage device 425, the system memory 415 is a volatile read-and-write memory, such as a random access memory. The system memory 415 stores some of the instructions and data that the processor needs at runtime. In some embodiments, the invention's processes are stored in the system memory 415, the permanent storage device 425, and/or the read-only 420. For example, the various memory units include instructions for processing appearance alterations of displayable characters in accordance with some embodiments. From these various memory units, the processing unit(s) 410 retrieves instructions to execute and data to process in order to execute the processes of some embodiments.

The bus 405 also connects to the input and output devices 430 and 435. The input devices enable the user to communicate information and select commands to the electronic system. The input devices 430 include alphanumeric keyboards and pointing devices (also called "cursor control devices"). The output devices 435 display images generated by the electronic system 400. The output devices 435 include printers and display devices, such as cathode ray tubes (CRT) or liquid crystal displays (LCD). Some embodiments include devices such as a touchscreen that functions as both input and output devices.

Finally, as shown in FIG. 4, bus 405 also couples electronic system 400 to a network 440 through a network adapter (not shown). In this manner, the computer can be a part of a network of computers (such as a local area network ("LAN"), a wide area network ("WAN"), or an intranet), or a network of networks (such as the Internet). Any or all components of electronic system 400 may be used in conjunction with the invention.

These functions described above can be implemented in digital electronic circuitry, in computer software, firmware or hardware. The techniques can be implemented using one or more computer program products. Programmable processors and computers can be packaged or included in mobile devices. The processes may be performed by one or more programmable processors and by one or more set of programmable logic circuitry. General and special purpose computing and storage devices can be interconnected through communication networks.

Some embodiments include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the invention has been described with reference to numerous specific details, one of ordinary skill in the art will recognize that the invention can be embodied in other specific forms without departing from the spirit of the invention. For instance, FIG. 1 conceptually illustrates a process. The specific operations of the process may not be performed in the exact order shown and described. Specific operations may not be performed in one continuous series of operations, and different specific operations may be performed in different embodiments. Furthermore, the process could be implemented using several sub-processes, or as part of a larger macro process. Thus, one of ordinary skill in the art would understand that the invention is not to be limited by the foregoing illustrative details, but rather is to be defined by the appended claims.

I claim:

1. A golf improvement system that identifies tools and training regimens that best assist a golfer to improve a golf swing, said golf improvement system comprising:
a web server computing device that is connected to the Internet and runs a web server software application that provides a golf improvement website hosted by the web server computing device, said golf improvement website accessible to computing devices of golfers who wish to improve their golf swings by interacting with the website to provide personal golf-related information that is aggregated by a crowd-sourcing software application that runs on the web server computing device;
a set of databases accessible to the crowd-sourcing software and the web server software, said set of databases storing the aggregated crowd-sourced golf-related information and the personal golf-related information received from each golfer; and
a computing device of a particular golfer, said computing device comprising a processor, a display device, and a golf improvement software application which when run on the processor of the computing device (i) connects to the web server, (ii) displays the golf improvement website on the display device, (iii) allows the particular golfer to interact with a set of GUI tools of the website to provide golf-related information associated with the particular golfer's own golf equipment and golf training regimen, and (iv) provides at least one best practice for improving the particular golfer's swing, said best practice based on an evaluation of the provided golf-related information in comparison with crowd-sourced golf-related information retrieved from the set of databases; and comprising a server computing device that is connected to the Internet and runs a golf tool and training regimen ranking software application that receives the aggregated personal golf-related information from the web server computing device, analyzes the aggregated personal golf-related information, and ranks the aggregated personal golf-related information.

2. The golf improvement system of claim 1, wherein the set of databases comprises a products database, a reviews database, a performance database, an instructors database, a practice database, and a rankings database.

3. The golf improvement system of claim 1, wherein the web server software application displays the ranked personal golf related information on the website.

4. The golf improvement system of claim 3, wherein the golf-related information associated with the particular golfer's own golf equipment and golf training regimen comprises a personal perspective of at least one of a training tool, a training regimen, a golf club, and an instructor.

5. The golf improvement system of claim 4, wherein the web server software application displays, on the website, the personal perspective in relation to the rank of the particular golfer's own golf equipment and golf training regimen.

6. A non-transitory computer readable medium storing a program which when executed by at least one processing unit of a computing device identifies golf-improving tools and training regimens that a golfer to improve one or more aspects of a golf game of the golfer, said program comprising sets of instructions for:

retrieving a set of golf improvements from a golf performance database, said golf improvements associated with a set of participating golf users;

ranking the set of golf improvements retrieved from the golf performance database;

retrieving a set of products from a golf products database, said golf products associated with the set of participating golf users;

analyzing the set of products in relation to the ranked set of golf improvements; and identifying a golf product from the set of products that led to a ranked golf improvement; and the program further comprises sets of instructions for;

retrieving a set of training regimens from a golf practice database, said training regimens associated with the set of participating golf users; and analyzing the set of training regimens in relation to the ranked set of golf improvements.

7. The non-transitory computer readable medium of claim 6, wherein the program further comprises a set of instructions for cross-aggregating the set of products and the set of training regimens in relation to the ranked set of golf improvements.

8. The non-transitory computer readable medium of claim 7, wherein the set of instructions for identifying comprises sets of instructions for identifying at least one cross-aggregated golf product and training regimen that led to a ranked golf improvement that satisfied a threshold improvement amount.

* * * * *